United States Patent [19]

Ragsdale et al.

[11] Patent Number: 5,612,489

[45] Date of Patent: Mar. 18, 1997

[54] ENHANCED SENSITIVITY FOR OXYGEN AND OTHER INTERACTIVE GASES IN SAMPLE GASES USING GAS CHROMATOGRAPHY

[75] Inventors: Daniel J. Ragsdale, Quakertown; George H. Smudde, Jr., Macungie; David A. Zatko, Lansdale, all of Pa.

[73] Assignee: Air Products and Chemicals, Inc., Allentown, Pa.

[21] Appl. No.: 601,627

[22] Filed: Feb. 14, 1996

[51] Int. Cl.$^6$ .................................................. G01N 30/34
[52] U.S. Cl. ........................... 73/23.35; 73/23.42; 422/89
[58] Field of Search ............................... 73/23.35, 23.41, 73/23.42, 23.37, 23.4, 24.02, 25.03; 422/89

[56] References Cited

U.S. PATENT DOCUMENTS

| | | | |
|---|---|---|---|
| 3,319,458 | 5/1967 | Curren | 73/23.35 |
| 4,713,362 | 12/1987 | Maroulis et al. | 502/85 |
| 4,744,805 | 5/1988 | Maroulis et al. | 55/66 |
| 4,747,854 | 5/1988 | Maroulis et al. | 55/66 |

*Primary Examiner*—Michael Brock
*Attorney, Agent, or Firm*—Geoffrey L. Chase

[57] ABSTRACT

The present invention is directed to a method of detecting trace levels of contained interactive gas, such as oxygen, in gases containing trace levels of interactive gas, such as oxygen, by doping a known low level amount of interactive gas (i.e., oxygen) into the detection apparatus to saturate interactive gas reactive or adsorptive sites in the apparatus, thus allowing the accurate, reproducible and responsive detection of contained interactive gas. More particularly, the present invention dopes a carrier gas of a gas chromatograph with low levels of oxygen in order to detect contained trace oxygen in a sample of a gas being analyzed for contained trace oxygen.

15 Claims, 3 Drawing Sheets

ENHANCED SENSITIVITY FOR OXYGEN AND OTHER INTERACTIVE GASES IN SAMPLE GASES USING GAS CHROMATOGRAPHY

TECHNICAL FIELD OF THE INVENTION

The present invention is directed to a method of detecting trace levels of contained interactive gases, such as oxygen, in gases containing trace levels of interactive gas by doping a known amount of the interactive gas into the detection apparatus to saturate interactive gas reactive or adsorptive sites in the apparatus, thus allowing the accurate and responsive detection of the contained interactive gas. More particularly, the present invention dopes a carrier gas of a gas chromatograph with low levels of oxygen in order to detect contained trace oxygen in a sample of a gas being analyzed for contained trace oxygen.

BACKGROUND OF THE INVENTION

The industrial gas industry is faced with ever more stringent requirements for purity in industrial gases for research and for industries, such as the electronic fabrication industry.

Oxygen is one of the contaminant gases for which tight specification requirements have been set by such industries, particularly for inert gases used for blanketing or prevention of oxidation. Oxygen impurity levels must be very low in such gases which are used for inerting atmospheres. Typically, those gases include nitrogen and argon. Other gases which face similar specifications include carbon monoxide, hydrogen, carbon dioxide, fluorine, chlorine and water.

In the purification, storage and dispensing of industrial gases, it is necessary to check or monitor purity on a batch or continuous basis. When the levels of impurities in gases is very low, such as parts per million (ppm) or parts per billion (ppb), and the monitoring of the gases for impurities is done in a batch or non-continuous basis, difficulties arise in having rapid, reproducible, accurate results. Effectively, it is difficult to reach a steady state condition.

Although it is possible to at least partially overcome this problem by using a dedicated analyzer, when the detection requires a sophisticated and/or expensive detection device, such as a gas chromatograph, the trend is to use such detection equipment for a plurality of analyses, so that it is impossible or impractical to reach a steady state for any particular impurity analysis.

The art has recognized that the adsorbent used in gas chromatographs for oxygen analysis can have improved performance if initially subjected to a singular oxidation treatment. This is reported in U.S. Pat. No. 4,744,805 and 4,713,362.

Removal of oxygen from bulk gases, in contrast to analysis, is described in U.S. Pat. No. 4,747,854.

The prior art has failed to achieve a solution to the problem of analysis of trace levels of interactive gases, such as oxygen, in gases requiring high purity specifications. The present invention provides an inexpensive method for trace level interactive gas, (i.e., oxygen,) impurity detection in gases using gas chromatography that is particularly valuable in non-steady state situations. The method is fast, accurate and sensitive to interactive gas, (i.e., oxygen), levels in the ppm and ppb range. This overcomes a problem that has existed for years that has prevented reproducible analysis.

BRIEF SUMMARY OF THE INVENTION

The present invention is a method for detecting trace levels of an interactive gas selected from the group consisting of oxygen, carbon monoxide, hydrogen, carbon dioxide, fluorine, chlorine and water, contained in a sample gas, which is mixed with a carrier gas, by detection of the interactive gas using a gas chromatograph in gas communication with a detector sensitive to the interactive gas, the improvement comprising doping the carrier gas with a low level of the interactive gas upstream of the detection.

Preferably, the sample gas is selected from the group consisting of hydrogen chloride, hydrogen bromide, arsine, phosphine, silane, nitrogen trifluoride, hexafluoroethane, trifluoromethane, nitrogen, argon, helium, hydrogen and mixtures thereof.

Preferably, the carrier gas is selected from the group consisting of helium, argon, nitrogen and mixtures thereof.

Preferably, the trace level of interactive gas in the sample gas is less than 1000 ppm.

More preferably, the trace level of interactive gas in the sample gas is less than 100 ppm.

Most preferably, the trace level of interactive gas in the sample gas is less than 1 ppm.

Preferably, the low level of interactive gas which is doped into the carrier gas results in less than 10 ppm interactive gas in the carrier gas.

More preferably, the low level of interactive gas which is doped into the carrier gas results in less than 1 ppm interactive gas in the carrier gas.

Most preferably, the low level of interactive gas which is doped into the carrier gas results in less than 100 ppb interactive gas.

Preferably, the low level of interactive gas is doped into the carrier gas by the method selected from the group consisting of dynamic dilution, permeation and calibrated leak.

Preferably, the detector sensitive to the interactive gas is selected from the group consisting of a thermoconductivity detector, a discharge ionization detector, a helium ionization detector, and a high frequency discharge detector.

Preferably, the gas chromatograph is packed with an adsorbent selected from the group consisting of zeolitic molecular sieves, porous polymers, silica gel, carbon molecular sieves and mixtures thereof.

Preferably, the low level of interactive gas is doped into the carrier gas upstream of a point of introduction of the sample gas into the carrier gas.

Alternatively, the low level of interactive gas is doped into the carrier gas downstream of a point of introduction of the sample gas into the carrier gas.

DETAILED DESCRIPTION OF THE INVENTION

Figure 1:
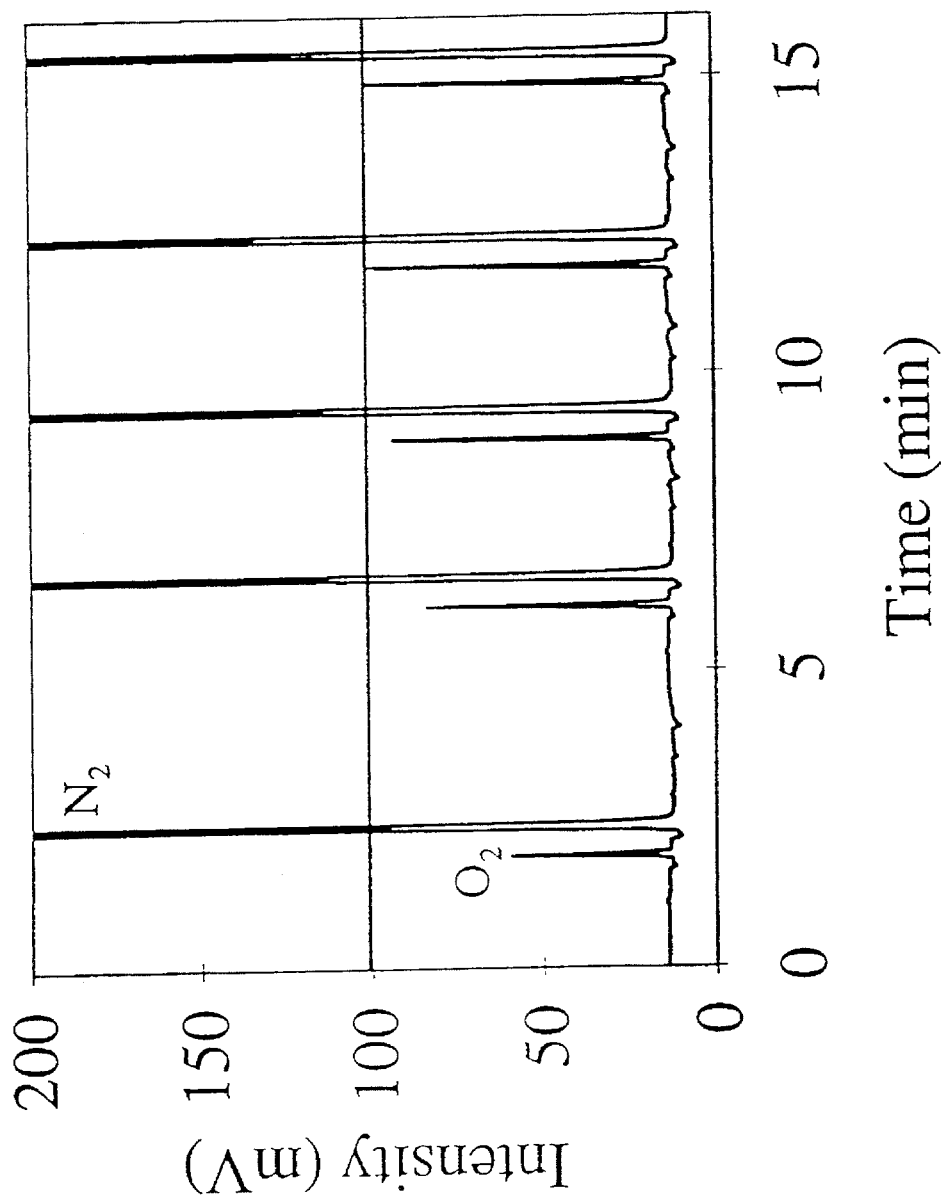
FIG. 1 is a gas chromatogram of a sample gas containing nitrogen and 3.9 ppm of oxygen in a helium carrier gas under the conditions of Example 1. Five separate injections are shown. Detected oxygen increases with subsequent injections.

The present inventors have determined that by doping the carrier gas to a gas chromatograph with interactive gas, such as oxygen, at a low level, typically less than 10 ppm (parts per million by volume), the detection of trace levels of the interactive gas, such as oxygen impurity in sample gases, such as bulk or specialty gases, can be improved.

Oxygen is the interactive gas that is most significant for trace detection in gases for the electronic industry, but other interactive gases, such as carbon monoxide, hydrogen, carbon dioxide, fluorine, chlorine and water can be analyzed by the present invention. The use of the term interactive is to indicate a gas that is reactive with or sorbed on the materials of construction of passageways, valves, and other equipment or column media (i.e., adsorbent) of the devices used for detection of the interactive gas to the point that the gas at the trace levels in which it is present in the sample gas is significantly or totally removed from the sample gas prior to detection so as to significantly alter or preclude accurate detection of the gas in the sample gas. Water is included in the interactive gases because of its ability to be present in trace quantities in the sample gas in the form of water vapor. When hydrogen is the sample gas, hydrogen would not be the trace interactive gas.

Typically industrial gases provided to demanding end uses, such as research or the electronics fabrication industry, have specifications which tolerate only very low levels of impurities or contaminants. It is difficult to detect impurities at the levels required by such end users. Oxygen is particularly difficult to detect at trace levels in other gases, because the present inventors have ascertained that low levels of oxygen are sorbed or chemically bound to various equipment surfaces so as not to be detected by the appropriate detector sensitive to oxygen, such as in a gas chromatograph. This is particularly problematic when the gas sampling ports and lines from the industrial gas source to be analyzed to the gas chromatograph are lengthy or convoluted. It is also problematic within the passageways of the gas chromatograph and the passageways leading from the gas chromatograph to the detector. Other interactive gases present the same problems.

Oxygen, particularly at trace levels less than 1000 ppm, can significantly or fully sorb on column packing, metal surfaces, plastics, Teflon fittings, etc. This can scavenge the oxygen impurity from the sample gas before it can be detected at the detector of a gas chromatograph. Various attempts have been made by the present inventors to use oxygen compatible materials of construction and highly finished materials to diminish oxygen sorption or reaction with such surfaces. The present inventors have also attempted to design sampling passageways, gas chromatograph hookups and gas chromatograph detector arrangements so as to diminish oxygen consumption (adsorption or reaction) in the gas chromatograph. They have also attempted to minimize areas where oxygen can hang-up, such as in eddy currents, deadspaces, etc. These attempts have typically resulted in inconsistent and temporary improvements in trace oxygen detection, and the speed and accuracy of trace oxygen detection, particularly in non-continuous sampling for trace oxygen. It is known that other interactive gases behave similarly.

Unexpectedly, the present inventors have found that by doping the carrier gas carrying the sample gas which is to be analyzed for trace oxygen with a known low level quantity (typically <10 ppm) of doping oxygen in the carrier gas, the detection limit for the trace oxygen impurity is greatly improved, along with the response time to achieve the detection. Potentially, the oxygen doping of the carrier gas can be at a level comparable to or less than the expected trace oxygen in the sample gas to be analyzed. This heightened sensitivity of the gas chromatograph and detector sensitive to trace oxygen impurity in a sample gas is contrary to what one would expect. For instance, one might expect that for trace levels of oxygen, adding oxygen might adversely interfere with the signal for the trace oxygen. Also, it is important to be able to closely regulate the doping rate. Uncontrolled or inconsistent doping of oxygen into the carrier gas will not result in greater sensitivity in gas chromatograph trace oxygen detection at very low trace oxygen levels. Consistent doping of oxygen into the carrier gas can be performed by dynamic dilution, permeation or calibrated leak or any other method which allows for precise, low level oxygen doping (typically <10 ppm, but potentially at the level of trace oxygen in the sample to be analyzed). Doping by dynamic dilution is performed by consistent mixing of the carrier gas with a stream containing either pure oxygen or a mixture of oxygen and the same gas as the carrier gas. Doping by permeation is performed by consistently diffusing oxygen from a separate reservoir through a material into the carrier gas. Doping using a calibrated leak is performed by constantly injecting a quantity of oxygen through controlled leak typically consisting of an orifice or capillary tube into the carrier gas. It is contemplated that other interactive gases can be handled in a similar manner. Alternatively, doping could be performed by using a mixture of carrier gas and the doping gas dispensed from an industrial gas cylinder.

Typically, it is appropriate to dope the interactive gas (i.e., oxygen) into the carrier gas upstream of the gas sampling valve or syringe injection point (point of introduction of sample gas) in a gas chromatograph. Alternatively, the interactive gas (i.e., oxygen) can be doped into the carrier gas downstream of the gas sampling valve (point of introduction). Downstream of the gas sampling valve is where non-continuous gas flow occurs, which can be problematic for interactive gas (i.e., oxygen) analysis. Doping can occur internal to the gas chromatograph, in a separate module attached to the gas chromatograph or in a separate module detached from the gas chromatograph.

The detector sensitive to the interactive gas (i.e., oxygen) is selected from the group consisting of a thermoconductivity detector, a discharge ionization detector, a helium ionization detector, and a high frequency discharge detector.

Although not wanting to be held to any particular theory, the present inventors believe that the doping of the carrier gas to the gas chromatograph with a calibrated, constant, low level (typically <10 ppm) of interactive gas (i.e., oxygen), allows the interactive gas (i.e., oxygen) to saturate or react with any sorptive or reactive sites in the passageways leading from the point of introduction of the carrier gas to the sample downstream to the detector sensitive to the interactive gas (i.e., oxygen). Therefore, the doping interactive gas (i.e., oxygen) eliminates the opportunity for the trace interactive gas (i.e., oxygen) from the sample gas being sorbed or reacted and provides a baseline background of interactive gas (i.e., oxygen) detection against which the spikes of the actual trace interactive gas (i.e., oxygen) in the sample gas being analyzed can be detected accurately and with fast response from when the sampling is actually performed.

Sample gases which can be analyzed for trace interactive gas such as oxygen by this method include: the bulk industrial gases; nitrogen, argon, helium and hydrogen, and the specialty industrial gases; hydrogen chloride, hydrogen bromide, arsine, phosphine, silane, nitrogen trifluoride, hexafluoroethane, trifluoromethane The doping interactive gas (i.e., oxygen) is preferably 99.999% by volume. Most preferably, the doping interactive gas (i.e., oxygen) is 99.9999% by volume. Alternatively, the low level of interactive gas (i.e., oxygen) in the carrier gas can be provided by a more dilute mixture of the interactive gas (i.e., oxygen) in the same gas as the carrier gas or other industrial gas.

The amount of doping interactive gas (i.e., oxygen) injected into the carrier gas is less than 10 ppm of interactive gas (i.e., oxygen) in the resulting doped carrier gas. Preferably, the range is less than 1 ppm. More preferably, the range is less than 100 ppb.

The carrier gas can be selected from the group comprising helium, argon and nitrogen.

This technique permits reproducible detection of trace interactive gas (i.e., oxygen) at quantities less than 1000 ppm. More preferably, it is useful to detect trace interactive gas (i.e., oxygen) of less than 100 ppm. Most preferably, it is useful in the range of less than 1 ppm. The values of ppm and ppb (parts per billion) are on a volumetric basis.

EXAMPLE 1

A sample containing 3.9 ppm $O_2$ and an undetermined amount of $N_2$ in He was analyzed in a gas chromatograph without using low level oxygen doping of the carrier gas (He) in a series of 5 sample injections within 15 minutes. The gas chromatograph was a Gow-Mac 590 with a 10 foot molecular sieve 5A analytical column and a discharge ionization detector (DID). The discharge current was 8.03 mA @ 600 v, the column flow rate was 31 standard cubic centimeters per minute (sccm) and the detector flow rate was 12 sccm. The sample size was 1 ml and the amplifier range was $10^{-12}$ with an attenuation of 1. FIG. 1 reports the results of the analysis and demonstrates the case where $O_2$ from the sample is not completely consumed by oxygen scavenging sites of the gas chromatograph. In this case, the peak area and height for $O_2$ is lowest after a period of time where the instrument has not analyzed a sample containing $O_2$. In subsequent injections, the $O_2$ peak areas and heights increase. The $O_2$ peak areas and heights from repeated injections attained constant values after 5 or more injections. This illustrates the added time required to reach a steady state so that accurate and consistent results can be obtained in a technique that does not use the methodology of the present invention.

EXAMPLE 2

Figure 2:
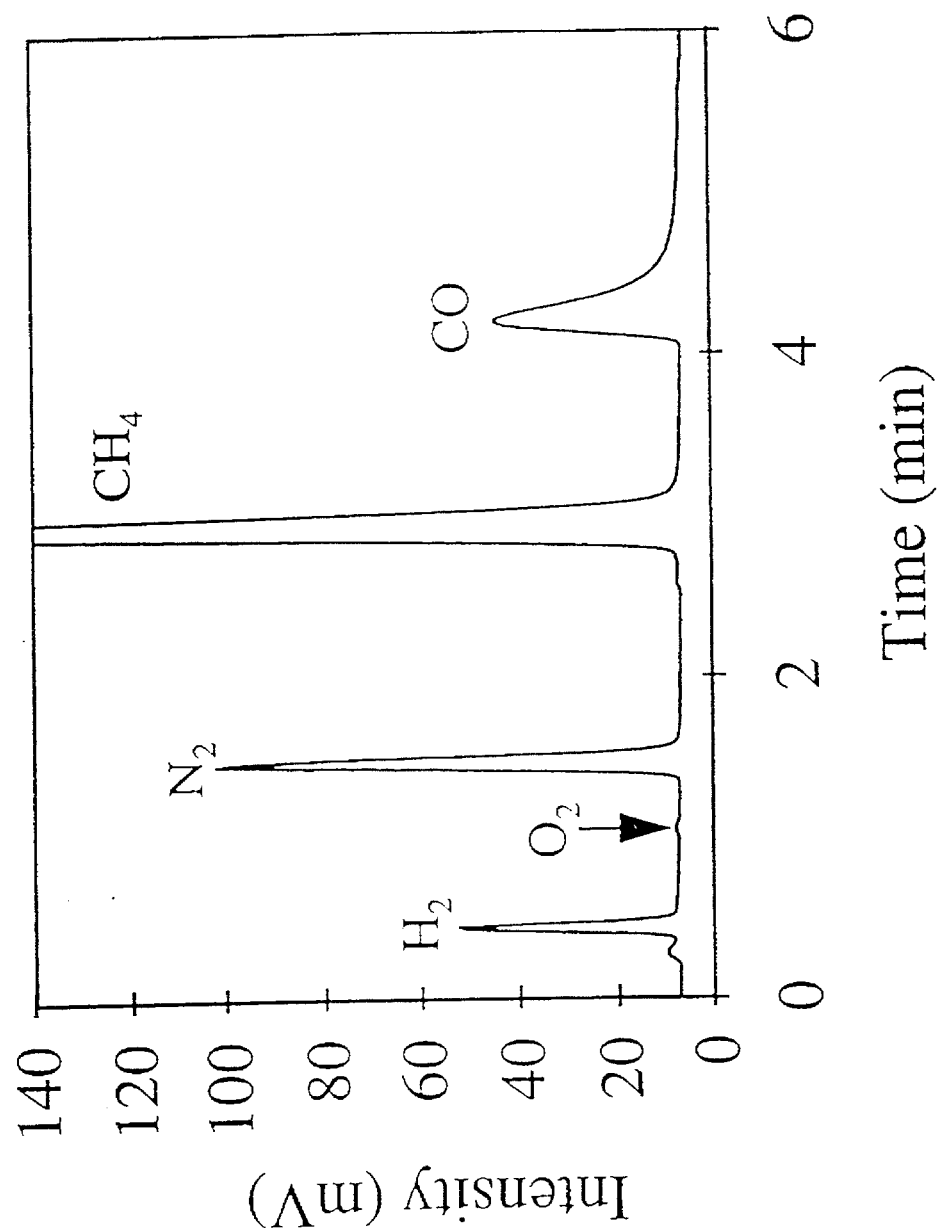
FIG. 2 is a gas chromatogram of a sample gas containing 2.4 ppm of oxygen in the sample recited in Example 2 in a helium carrier gas. One injection is shown because all injections resulted in the same oxygen response. Oxygen remains undetected.

A sample containing 1.9 ppm $H_2$, 2.4 ppm $O_2$, 1.9 ppm $N_2$, 2.0 ppm $CH_4$, 2.1 ppm CO in He was subjected to analysis in a gas chromatograph without doping of the carrier gas with low levels of oxygen. The gas chromatograph was a Gow-Mac 590 with a 6 foot molecular sieve 5A analytical column and a discharge ionization detector (DID). The column flow rate was 29 sccm and the detector flow rate was 11 sccm. The sample size was 1 ml and the amplifier range was $10^{-12}$ with an attenuation of 1. The gas chromatograph analysis of oxygen in the sample gas contained in the He carrier gas is illustrated in FIG. 2 for one of several injections of the sample into the gas chromatograph. In this instance, the sample containing 2.4 ppm $O_2$ gave no appreciable peak, even after repeated injections over a period of time. Apparently, almost all $O_2$ is consumed by the gas chromatograph system, and subsequent injections did not increase the peak area or height. Quantification of trace $O_2$ under these conditions is not possible.

EXAMPLE 3

Figure 3:
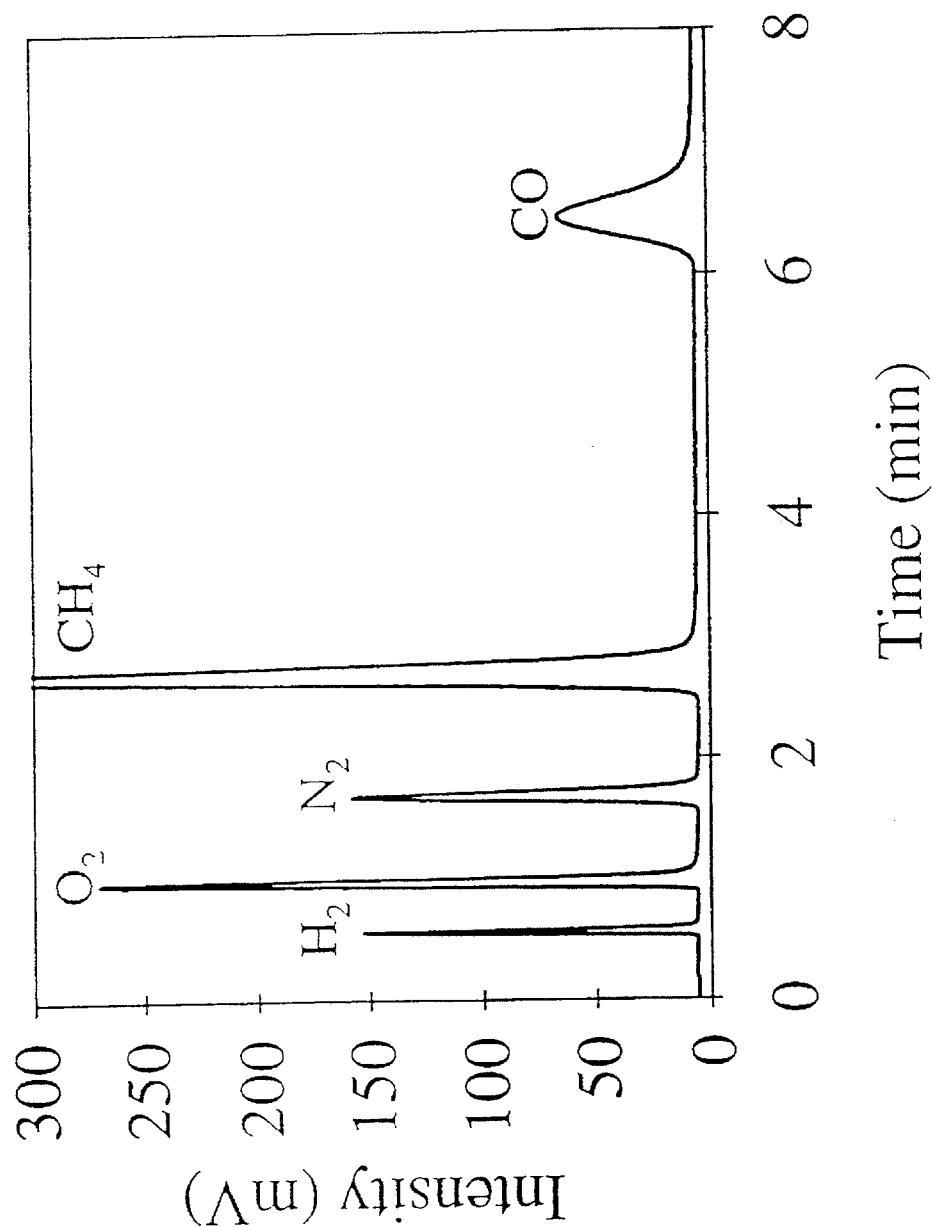
FIG. 3 is a gas chromatogram of the sample gas of Example 3 containing 5.8 ppm of oxygen in a helium carrier gas and using low level oxygen doping of that carrier gas. One injection is shown.

An experiment was conducted using the procedure outlined in the present invention of low level oxygen doping of the sample's carrier gas. The sample contained 5.3 ppm $H_2$, 5.8 ppm $O_2$, 6.3 ppm $N_2$, 4.9 ppm $CH_4$, and 5.1 ppm CO in He. Table 1 shows the reported peak areas for the seven injections of the sample gas doped with 5.8 ppm $O_2$ in the He carrier gas after the gas chromatograph instrument was idle overnight. Each oxygen analysis is very consistent with the other analyses in the experiment. FIG. 3 shows the resulting chromatogram for one of the analyses. The peak area for $O_2$ is large and results are consistent for multiple analyses. These data were obtained on the same gas chromatograph as Examples 1 and 2. The column flow rate was 32 sccm and the detector flow rate was 15 sccm. The analytical column was a 3 foot molecular sieve 13X and the precolumn was 3 ft silica gel. The sample size was 1 ml and the amplifier range was $10^{-12}$ with an attenuation of 1. This example demonstrates that when the present invention is implemented, high consistent $O_2$ sensitivity is attained.

TABLE 1

| $O_2$ Peak Area (mA · sec) |
| --- |
| 1057 |
| 1056 |
| 1054 |
| 1056 |
| 1056 |
| 1059 |
| 1056 |

EXAMPLE 4

A 1 ml sample of helium containing oxygen at a flow rate of 100 sccm was further used to test the method of oxygen doping. Oxygen was doped into a helium carrier gas of a gas chromatograph at a low level of 26 parts per billion (ppb) of oxygen in the carrier gas. The oxygen was doped by using a Kin-Tek Laboratories permeation cell. The cell was maintained at room temperature during the doping and the oxygen content of the carrier gas was determined by the partial pressure of the oxygen in the cell. The oxygen level was confirmed with a Delta F Nanotrace oxygen analyzer. The detector was a discharge ionization detector and the discharge current was 8.0 mA at 600 V. The oxygen doped helium carrier gas was passed through a 13X molecular sieve analytical column at 32° C. at a flowrate of 30 cc/min. The lowest measured value for oxygen was 23 ppb and the limit of detection was 17 ppb. Under the same conditions, the limits of detection for hydrogen, nitrogen, methane and carbon monoxide were 12, 24, 6, and 40 ppb, respectively.

As can be seen from the above example, the method of the present invention is a significant improvement in the art of detecting trace interactive gas, preferably oxygen, in sampled gases containing interactive gas (i.e., oxygen) in trace quantities. The method of the present invention provides fast, sensitive and reproducible detection of interactive gas (i.e., oxygen) at trace levels below 1000 ppm.

The prior art has attempted to overcome the problem of trace interactive gas (i.e., oxygen) detection by designing systems with less interactive gas (i.e., oxygen) receptive surfaces, by designing systems with less travel distance or by using repetitious detection samplings. These attempts have not been successful in achieving a sensitive, quick, low level interactive gas (i.e., oxygen) detection methodology, particularly for batch or non-continuous sampling. The present invention overcomes the drawbacks of the prior art by providing interactive gas, preferably oxygen, doping of the carrier gas of a gas chromatograph to successfully achieve sensitive, rapid, low level detection of trace interactive gas, preferably oxygen, in sampled gases, even in batch or non-continuous samplings.

The present invention has been described with regard to several preferred embodiments, however the scope of the present invention should be ascertained from the claims which follow.

We claim:

1. A method for detecting trace levels of an interactive gas selected from the group consisting of oxygen, carbon monoxide, hydrogen, carbon dioxide, fluorine, chlorine and water, contained in a sample gas, which is mixed with a carrier gas, by detection of said interactive gas using a gas chromatograph in gas communication with a detector sensitive to said interactive gas, the improvement comprising doping said carrier gas with a low level of said interactive gas prior to said detection.

2. The method of claim 1 wherein said sample gas is selected from the group consisting of hydrogen chloride, hydrogen bromide, arsine, phosphine, silane, nitrogen trifluoride, hexafluoroethane, trifluoromethane, nitrogen, argon, helium, hydrogen and mixtures thereof.

3. The method of claim 1 wherein said carrier gas is selected from the group consisting of helium, argon, nitrogen and mixtures thereof.

4. The method of claim 1 wherein said trace level of interactive gas in said sample gas is less than 1000 ppm.

5. The method of claim 1 wherein said trace level of interactive gas in said sample gas is less than 100 ppm.

6. The method of claim 1 wherein said trace level of interactive gas in said sample gas is less than 1 ppm.

7. The method of claim 1 wherein said low level of interactive gas which is doped into said carrier gas is less than 10 ppm.

8. The method of claim 1 wherein said low level of interactive gas which is doped into said carrier gas is less than 1 ppm.

9. The method of claim 1 wherein said low level of interactive gas which is doped into said carrier gas is less than 100 ppb.

10. The method of claim 1 wherein said low level of interactive gas is doped into said carrier gas by the method selected from the group consisting of dynamic dilution, permeation and calibrated leak.

11. The method of claim 1 wherein said detector sensitive to said interactive gas is selected from the group consisting of a thermoconductivity detector, a discharge ionization detector, a helium ionization detector, and a high frequency discharge detector.

12. The method of claim 1 wherein said gas chromatograph is packed with an adsorbent selected from the group consisting of zeolitic molecular sieves, porous polymers, silica gel, carbon molecular sieves and mixtures thereof.

13. The method of claim 1 wherein said low level of interactive gas is doped into said carrier gas downstream of a point of introduction of said sample gas into said carrier gas.

14. The method of claim 1 wherein said low level of interactive gas is doped into said carrier gas upstream of a point of introduction of said sample gas into said carrier gas.

15. A method for detecting trace levels of oxygen in a sample gas, which is mixed with a carrier gas, by detection of said oxygen using a gas chromatograph in gas communication with a detector sensitive to oxygen, the improvement comprising doping said carrier gas with a low level of oxygen prior to said detection.

* * * * *